United States Patent
Hoang

(10) Patent No.: US 10,266,561 B2
(45) Date of Patent: Apr. 23, 2019

(54) METHOD FOR SEPARATING PROTEINS FROM ANIMAL OR HUMAN PLASMA, OR PLANTS, USING A PH GRADIENT METHOD

(71) Applicant: Kieu Hoang, Westlake Village, CA (US)

(72) Inventor: Kieu Hoang, Westlake Village, CA (US)

( * ) Notice: Subject to any disclaimer, the term of this patent is extended or adjusted under 35 U.S.C. 154(b) by 0 days.

(21) Appl. No.: 15/278,699

(22) Filed: Sep. 28, 2016

(65) Prior Publication Data

US 2017/0233434 A1  Aug. 17, 2017

Related U.S. Application Data

(60) Provisional application No. 62/233,913, filed on Sep. 28, 2015.

(51) Int. Cl.
| | |
|---|---|
| *C07K 1/14* | (2006.01) |
| *A61K 9/16* | (2006.01) |
| *A61K 38/17* | (2006.01) |
| *C07K 1/34* | (2006.01) |
| *C07K 14/47* | (2006.01) |
| *A61K 35/16* | (2015.01) |
| *C07K 1/00* | (2006.01) |
| *C07K 16/06* | (2006.01) |
| *C07K 1/30* | (2006.01) |

(52) U.S. Cl.
CPC ............... *C07K 1/14* (2013.01); *A61K 9/16* (2013.01); *A61K 35/16* (2013.01); *A61K 38/1709* (2013.01); *C07K 1/00* (2013.01); *C07K 1/145* (2013.01); *C07K 1/30* (2013.01); *C07K 1/34* (2013.01); *C07K 14/47* (2013.01); *C07K 16/065* (2013.01)

(58) Field of Classification Search
None
See application file for complete search history.

(56) References Cited

U.S. PATENT DOCUMENTS

| | | | | |
|---|---|---|---|---|
| 2007/0055055 A1* | 3/2007 | Sang | ............... | C07K 1/18 530/414 |
| 2009/0286960 A1* | 11/2009 | Hoang | ............... | C07K 14/775 530/359 |
| 2012/0177610 A1* | 7/2012 | Hoang | ............... | A61K 38/1709 424/93.7 |
| 2014/0142284 A1* | 5/2014 | Hoang | ............... | A61K 38/1709 530/359 |
| 2014/0343253 A1* | 11/2014 | Van Alstine | ............... | C07K 1/30 530/362 |

OTHER PUBLICATIONS

PCT/US16/54120 International Preliminary Report on Patentability, dated Jan. 19, 2017.

\* cited by examiner

*Primary Examiner* — Maury A Audet
(74) *Attorney, Agent, or Firm* — Merek, Blackmon & Voorhees, LLC

(57) ABSTRACT

The present subject matter is directed to a method for separating proteins of plasma using pH adjustment including the steps of reconstituting Fraction III, Fraction IV, or plasma paste, in water for injection; adjusting pH value to 1 and temperature from 1° C. to 30° C.; centrifuging the resulting suspension at 6,000 rpm at 2-8° C. for 20 min; collecting the resulting paste 1 (P1) and supernatant 1 (S1); reconstituting P1 in WFI and adjust the pH to 2; and repeating step 3) to step 5) until the pH of supernatant reaches 14. According to the method, a new formulation of immunoglobulin is prepared from plasma Fraction III and Fraction IV.

4 Claims, 6 Drawing Sheets

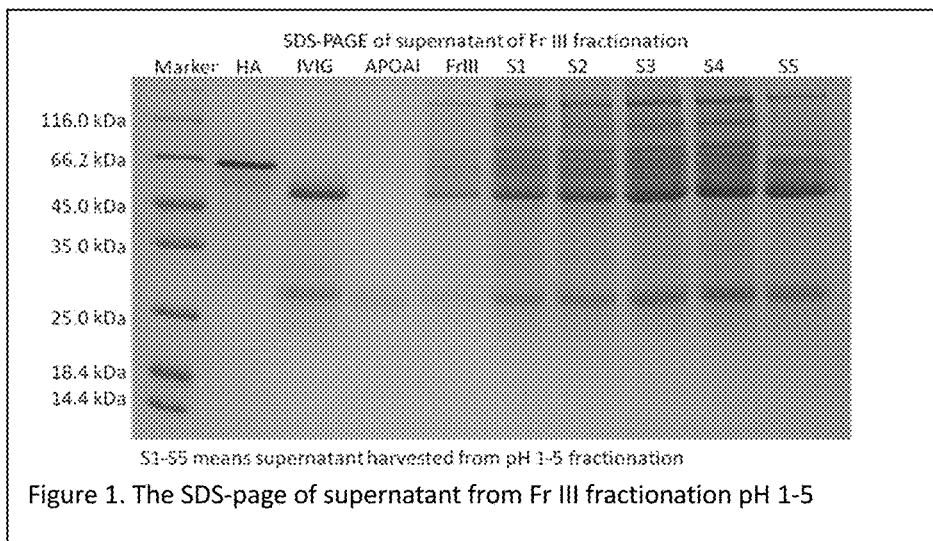
Figure 1. The SDS-page of supernatant from Fr III fractionation pH 1-5
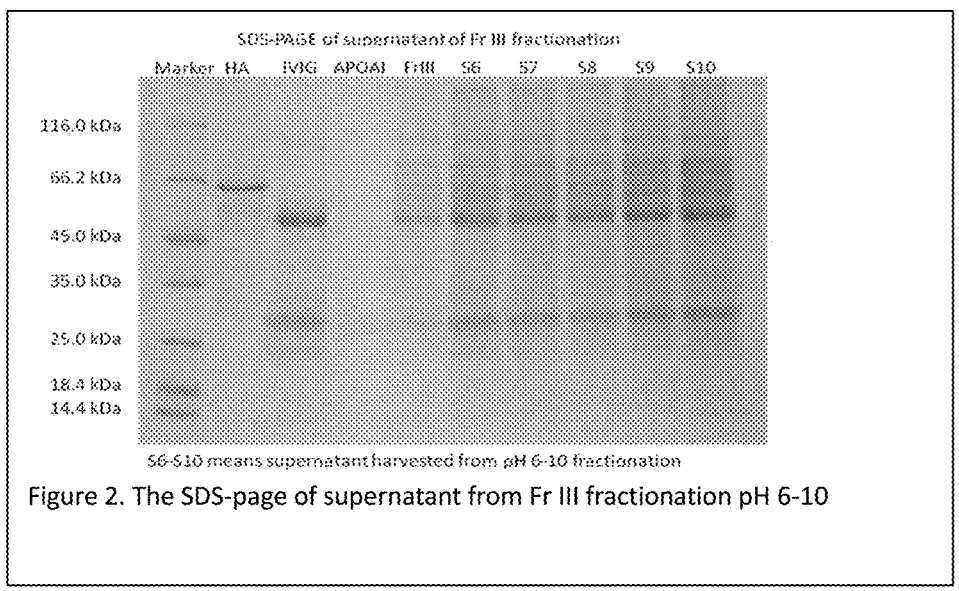
Figure 2. The SDS-page of supernatant from Fr III fractionation pH 6-10

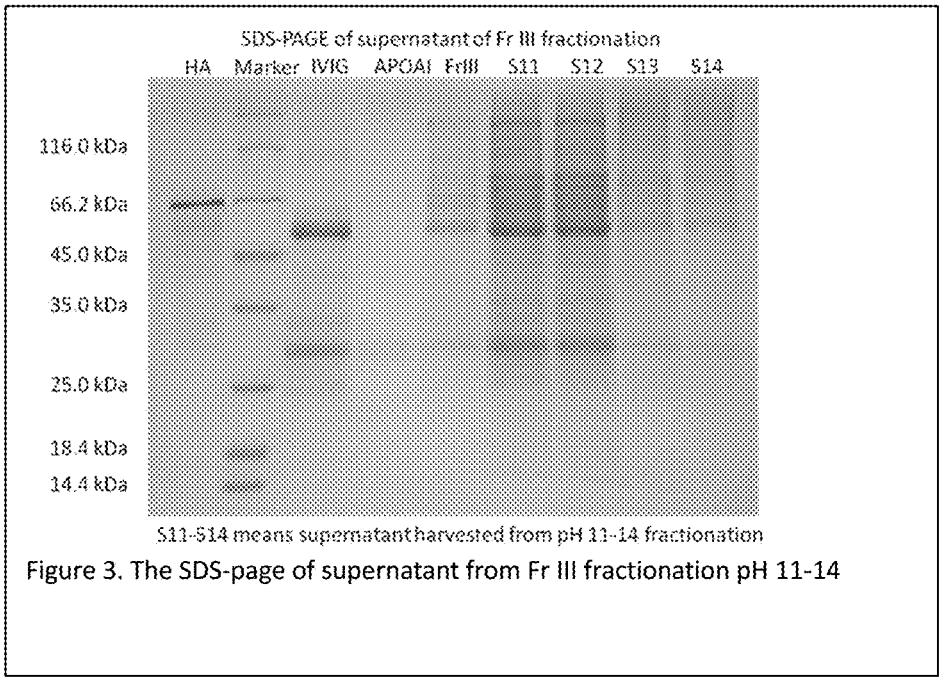
Figure 3. The SDS-page of supernatant from Fr III fractionation pH 11-14
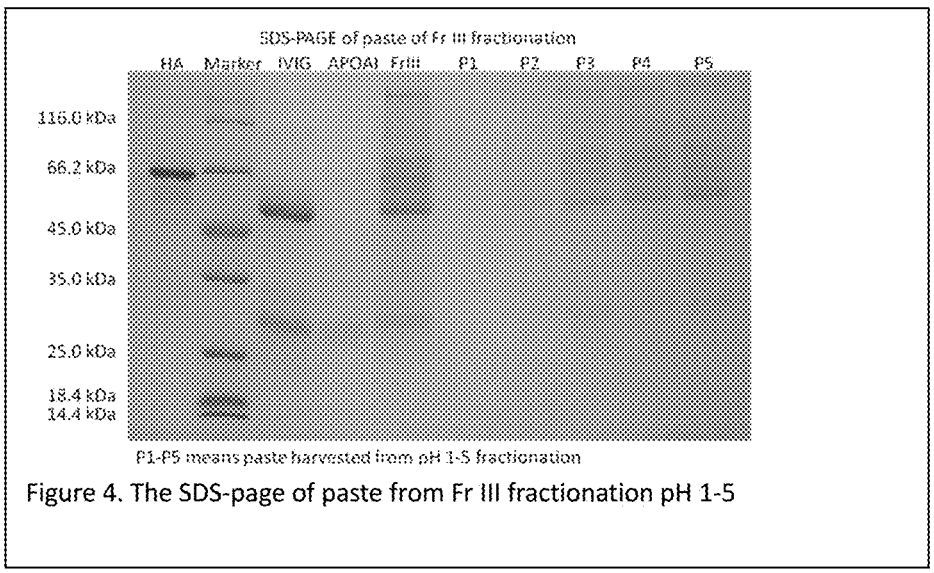
Figure 4. The SDS-page of paste from Fr III fractionation pH 1-5

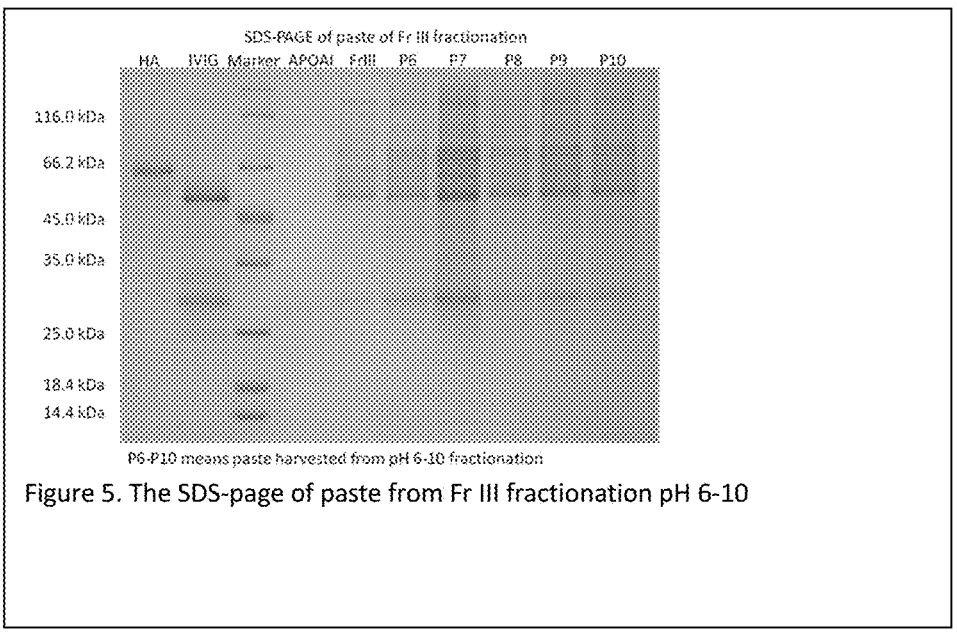
Figure 5. The SDS-page of paste from Fr III fractionation pH 6-10
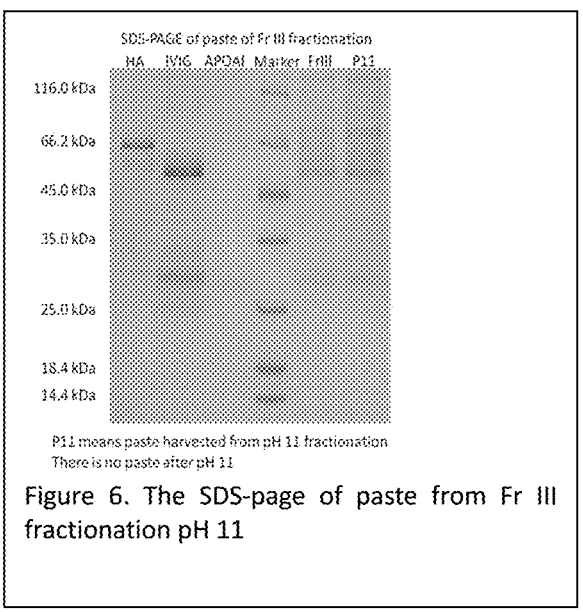
Figure 6. The SDS-page of paste from Fr III fractionation pH 11

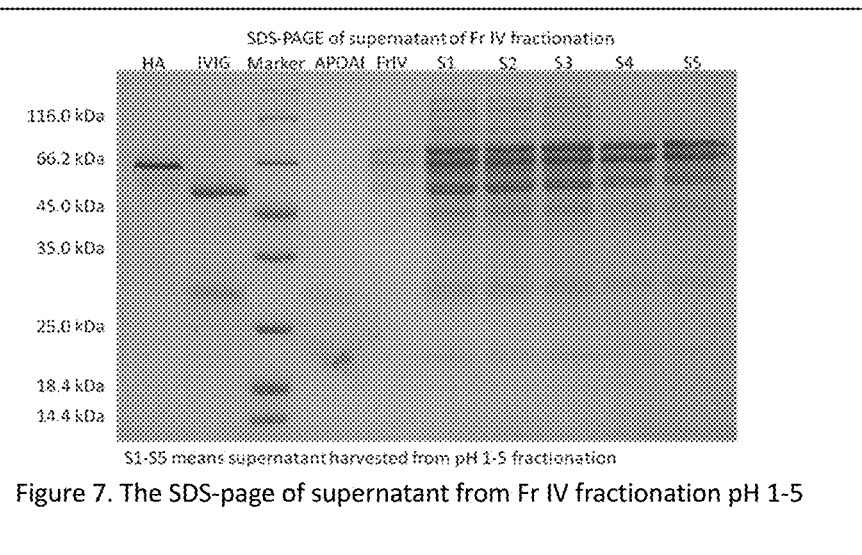
Figure 7. The SDS-page of supernatant from Fr IV fractionation pH 1-5
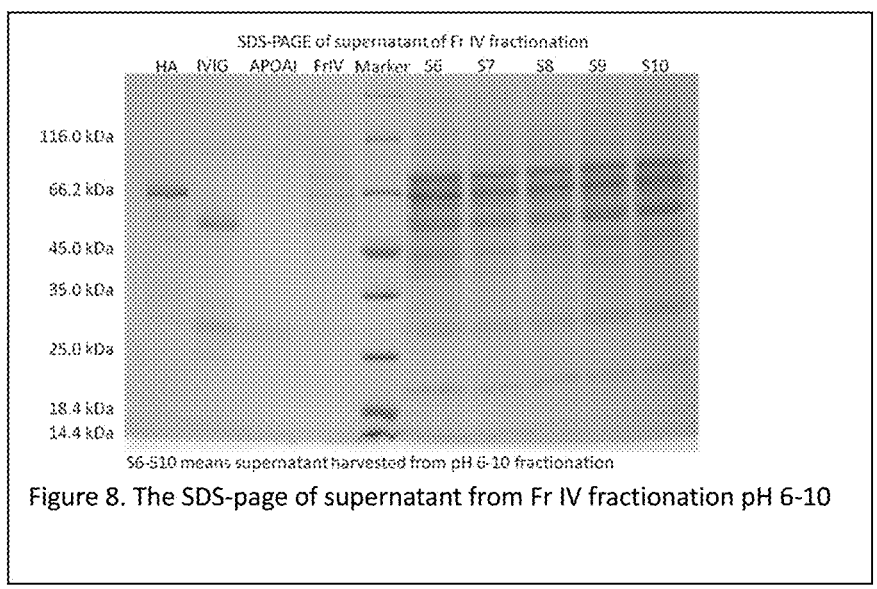
Figure 8. The SDS-page of supernatant from Fr IV fractionation pH 6-10

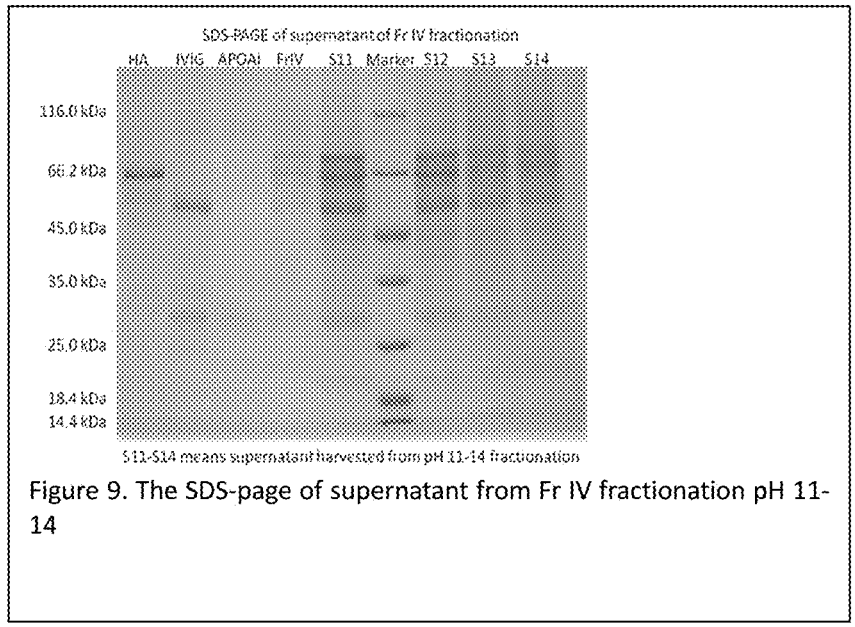
Figure 9. The SDS-page of supernatant from Fr IV fractionation pH 11-14
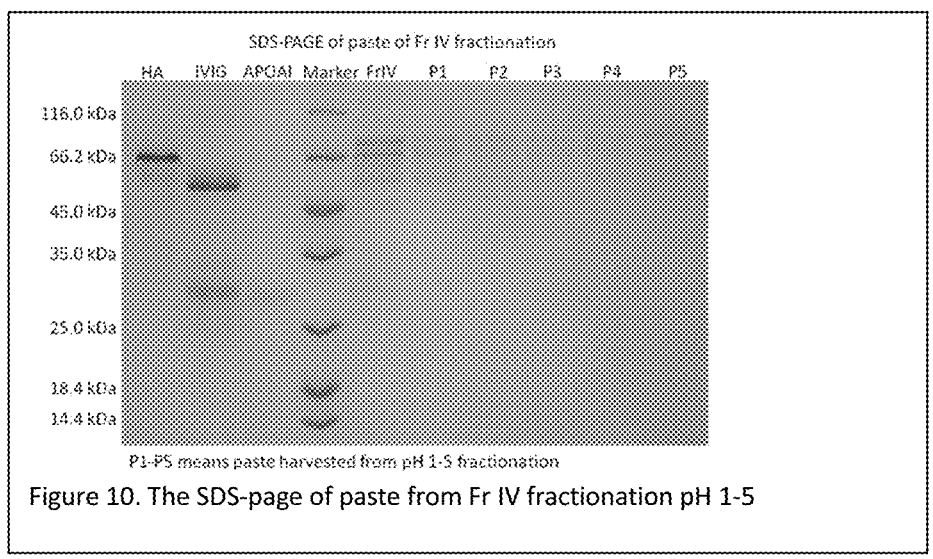
Figure 10. The SDS-page of paste from Fr IV fractionation pH 1-5

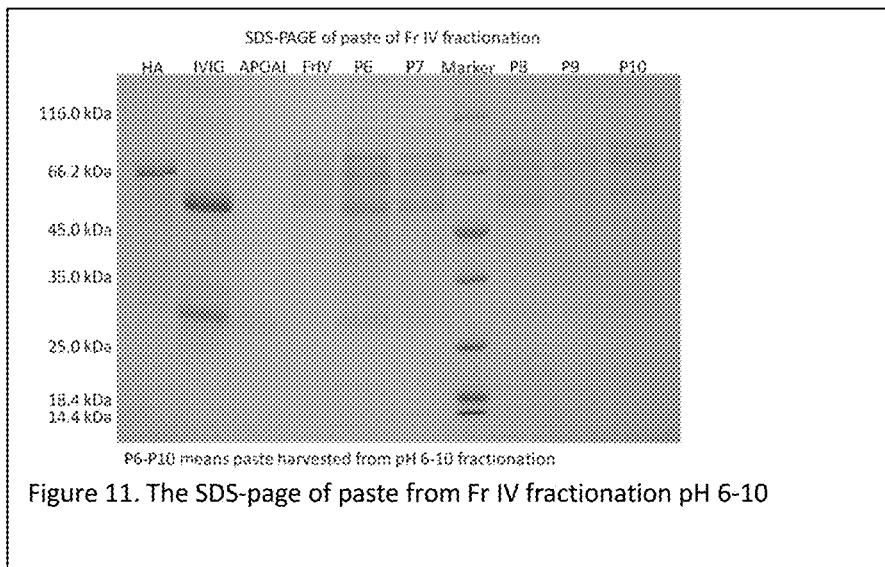
Figure 11. The SDS-page of paste from Fr IV fractionation pH 6-10
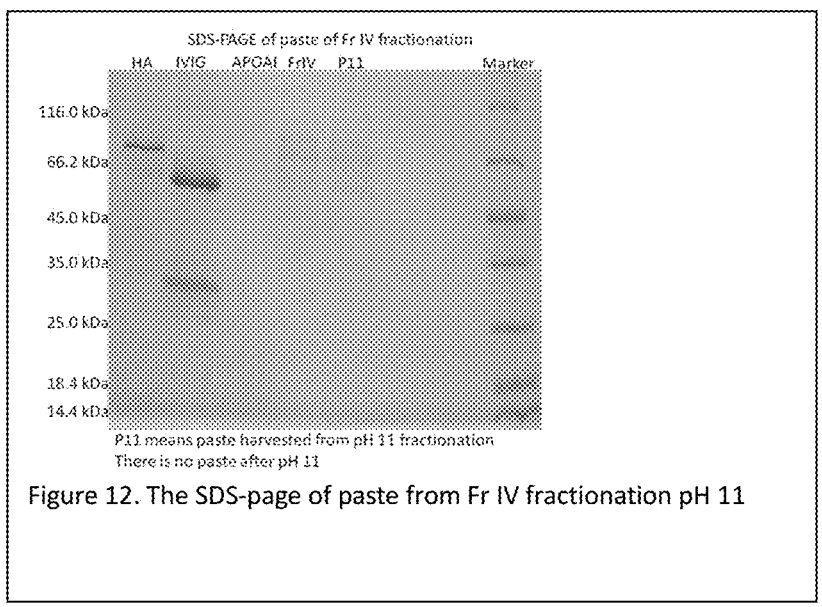
Figure 12. The SDS-page of paste from Fr IV fractionation pH 11

METHOD FOR SEPARATING PROTEINS FROM ANIMAL OR HUMAN PLASMA, OR PLANTS, USING A PH GRADIENT METHOD

CROSS-REFERENCE TO RELATED APPLICATIONS

This application claims the benefit of U.S. Provisional Application No. 62/233,913 filed on Sep. 28, 2015. The above-identified patent application is herein incorporated by reference in its entirety to provide continuity of disclosure.

FIELD

The present subject matter relates to a method of fractionation of plasma, and more particularly, to a method of fractionating plasma using a pH gradient process to separate proteins.

BACKGROUND

The Cohn Cold Fractionation Process ("Cohn Process") is generally employed in the fractionation of plasma into a number of medically useful and important protein fractions in addition to the production of albumin. The Cohn Process involves modifying the pH, ethanol concentration, and temperature to separate proteins through precipitation into five "fractions". The separated proteins then undergo an extensive purification process that includes cryoprecipitation, nanofiltration, solvent detergent treatments, and incubation, to produce a sterile, virally inactivated protein product.

In particular, Immunoglobulin G (IgG) is a type of antibody and is a protein complex composed of four peptide chains—two identical heavy chains and two identical light chains arranged in a Y-shape typical of antibody monomers. Each IgG has two antigen binding sites. Representing approximately 75% of serum antibodies in humans, IgG is the most common type of antibody found in the circulatory system. IgG molecules are typically created and released by plasma B cells. Antibodies are major components of humoral immunity. IgG is the main type of antibody found in blood and extracellular fluid, allowing it to control infection of body tissues. IgG protects the body from infection by binding many kinds of pathogens, such as viruses, bacteria, and fungi. In the plasma-derived industry, IgG is usually purified from human plasma from Fraction II. However, a certain percentage of IgG may be precipitated from Fraction III paste, which includes 34 existing and newly-found proteins, and 55 new found proteins in fractions of plasma.

Typically, Fraction IV is a discard fraction in the plasma derived products industry. It mainly contains human albumin, apolipoprotein, transferrin, alpha 1 antitrypsin haptoglobin, vimentin and new found proteins. One particular product, AFOD, contains 15 human proteins in which there are 4 new found proteins in the fractions of plasma.

SUMMARY

The present subject matter has been made in view of the above circumstances, and an object of the present subject matter is to provide a method for separating proteins of animal or human plasma Fraction III, Fraction IV, plasma, or plants, using pH adjustment. The present subject matter provides a method for separating proteins of fractions of plasma using pH adjustment and water for injection, without the use of alcohol or other buffers. Use of the present subject matter simplifies the process for separating fractions of plasma and prevents denaturation of proteins by conventional processes such as the Cohn Process.

According to one embodiment of the present subject matter, a method to separate proteins from animal or human plasma Fraction III, Fraction IV, plasma, or plants using a pH gradient method is provided. Therefore, a new formulation of immunoglobulin can be prepared from Fraction III, which has 34 existing and unknown new found proteins among which 14 are new found proteins, and 55 new found proteins in the fractions of plasma. The present subject matter can not only stop replication of Hepatitis C virus, but also kill Hepatitis C Virus and, ultimately, eradicate Hepatitis C virus infection.

In another embodiment of the present subject matter, a method to fractionate plasma Fraction IV with pH adjustment is provided. Therefore, a new formulation of AFOD and other products, containing 15 human proteins in which there are 4 new found proteins, can be prepared from Fraction IV using the present method. The present subject matter can not only stop replication of HIV-1 and HIV-2 viruses, but also kill HIV-1 and HIV-2 viruses and, ultimately, eradicate HIV-1 and HIV-2 virus infection.

An embodiment of the present subject matter is directed to a method of separating proteins from fractions of plasma using a pH gradient process, comprising the steps:
a. reconstituting a Fraction III, Fraction IV or plasma paste in water for injection;
b. adjusting pH value to 1 and temperature from 1° C. to 30° C. to form a resultant suspension;
c. centrifuging the resultant suspension at 6,000 rpm at 2-8° C. for 20 min;
d. collecting a resulted paste (P1) and supernatant 1 (S1);
e. reconstituting P1 in water for injection and raising the pH value by 1;
f. repeating steps b) to step e) until the pH of S1 reaches 14 to form a resulting solution;
g. adjusting the protein concentration and pH of the resulting solution;
h. subjecting the resulting solution to 0.22 um aseptic filtration and 20 nm nano-filtration for virus removal; and
i. subjecting the resulting solution to filling and low pH incubation at a pH of 4 for 21 days at 25° C. as a second virus inactivation.

Another embodiment of the present subject matter is directed to a further method of separating proteins from fractions of plasma using a pH gradient process, comprising the steps:
1) reconstituting a Fraction III, a Fraction IV, or a plasma paste in water for injection ("WFI") to a suspension, and adjusting the suspension to an initial pH value of 1;
2) adjusting the suspension to a temperature lower than 30° C.; 3) centrifuging the suspension at 6,000 rpm at 2-8° C. for at least 20 min; 4) collecting a resulting paste 1 (P1) and supernatant 1 (S1) from the centrifuged suspension;
5) reconstituting the P1 in WFI and raising the pH of the P1 by 1; and
6) repeating step 3) to step 5) until the pH of S1 reaches 14 to form a solution; wherein the Fraction III, Fraction IV, or plasma paste is obtained by pH adjustment in water for injection without requiring alcohol or other buffers for protein separation.

BRIEF DESCRIPTION OF THE DRAWINGS

Many aspects of the disclosure can be better understood with reference to the following figures.

FIG. 1 shows a sodium dodecyl sulphate-polyacrylamide gel electrophoresis (SDS-PAGE) of supernatant from Fraction III fractionation at a pH from 1-5.

FIG. 2 shows a SDS-PAGE of supernatant from Fraction III fractionation at a pH from 6-10.

FIG. 3 shows a SDS-PAGE of supernatant from Fraction III fractionation at a pH from 11-14.

FIG. 4 shows a SDS-PAGE of paste from Fraction III fractionation at a pH from 1-5.

FIG. 5 shows a SDS-PAGE of paste from Fraction III fractionation at a pH from 6-10.

FIG. 6 shows a SDS-PAGE of paste from Fraction III fractionation at a pH of 11.

FIG. 7 shows a SDS-PAGE of supernatant from Fraction IV fractionation at a pH from 1-5.

FIG. 8 shows a SDS-PAGE of supernatant from Fraction IV fractionation at a pH from 6-10.

FIG. 9 shows a SDS-PAGE of supernatant from Fraction IV fractionation at a pH from 11-14

FIG. 10 shows a SDS-PAGE of paste from Fraction IV fractionation at a pH from 1-5.

FIG. 11 shows a SDS-PAGE of supernatant from Fraction IV fractionation at a pH from 6-10.

FIG. 12 shows a SDS-PAGE of supernatant from Fraction IV fractionation at a pH of 11.

DETAILED DESCRIPTION

Unless defined otherwise all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language; however, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

According to one embodiment of the present subject matter, a method for separating proteins from fractions of plasma using a pH gradient process is provided. The method provides a process to fractionate plasma Fraction III, Fraction IV, plasma, or plants, comprising the steps of:

a. reconstituting Fraction III, Fraction IV or plasma paste, in water for injection;
b. adjusting pH value to 1 and temperature from 1° C. to 30° C. to form a resulting suspension;
c. centrifuging the resulting suspension at 6,000 rpm at 2-8° C. for 20 min;
d. collecting a resulting paste (P1) and supernatant 1 (S1);
e. reconstituting P1 in water for injection and raising the pH by 1; and
f. repeating steps b) to step e) until the pH of S1 reaches 14 to form a resulting solution.

In some embodiments, the method may further include the following steps:

a. adjusting the protein concentration and pH of the resulting solution;
b. subjecting the resulting solution to 0.22 um aseptic filtration and 20 nm nano-filtration for a first virus inactivation; and
c. subjecting the resulting solution to filling and low pH incubation at a pH of 4 for 21 days at 25° C. as a second virus inactivation.

As shown in FIGS. 1-12, the method of separating proteins of plasma Fraction III and Fraction IV using a pH gradient process improves the effectiveness of the separation of proteins during plasma fractionation. In this respect, sodium dodecyl sulphate-polyacrylamide gel electrophoresis (SDS-PAGE) was used in order to separate proteins of plasma Fractions III and IV based on their molecular weight at different pH levels according to the pH gradient method. The SDS-PAGE results provide the average molecular weight of both the supernatant and the paste of Fractions III and IV.

In this respect, FIGS. 1-3 show the SDS-PAGE of the supernatant from Fraction III fractionation at a pH of 1-5, 6-10 and 11-14, respectively.

FIGS. 4-6 show the SDS-PAGE of the paste from Fraction III fractionation at a pH of 1-5, 6-10 and 11-14, respectively.

FIGS. 7-9 show the SDS-PAGE of supernatant from Fraction IV fractionation at a pH of 1-5, 6-10 and 11-14, respectively.

FIGS. 10-12 show the SDS-PAGE of paste from Fraction IV fractionation at a pH of 1-5, 6-10 and 11-14, respectively.

An embodiment of the present subject matter is directed to a method of stopping replication of HIV-1 and HIV-2 in a patient comprising administering Fraction IV obtained from the present method to a patient in need thereof.

Another embodiment of the present subject matter provides a method of preventing infection of Hepatitis C virus in a patient comprising administering Fraction III obtained from the present method to a patient in need thereof.

Any of these fractions or any combination of the new found proteins have the following abilities:

1) transform/repair damaged and sick cells to become good healthy cells;
2) protect cellular alterations; and
3) signal the body to produce new healthy cells immunized from intra- and extracellular damaging signals.

With the information contained herein, various departures from precise descriptions of the present subject matter will be readily apparent to those skilled in the art to which the present subject matter pertains, without departing from the spirit and the scope of the below claims. The present subject matter is not considered limited in scope to the procedures, properties, or components defined, since the preferred embodiments and other descriptions are intended only to be illustrative of particular aspects of the presently provided subject matter. Indeed, various modifications of the described modes for carrying out the present subject matter which are obvious to those skilled in chemistry, biochemistry, or related fields are intended to be within the scope of the following claims.

What is claimed is:

1. A method for separating proteins of plasma using pH adjustment, the method comprising the steps of:
   1) reconstituting a Fraction III, a Fraction IV, or a plasma paste in water for injection ("WFI") to a suspension, and adjusting the suspension to an initial pH value of 1;
   2) adjusting the suspension to a temperature lower than 30° C.;
   3) centrifuging the suspension at 6,000 rpm at 2-8° C. for at least 20 minutes;
   4) collecting a resulting paste 1 (P1) and supernatant 1 (S1) from the centrifuged suspension;
   5) reconstituting the P1 in WFI and raising the pH of the P1 by 1; and
   6) repeating step 3) to step 5) until the pH of S1 reaches 14 to form a solution;
   wherein the Fraction III, Fraction IV, or plasma paste is obtained by pH adjustment in water for injection without requiring alcohol or other buffers for protein separation.

2. The method of claim 1, wherein the resulting Fraction III, Fraction IV, or plasma paste is re-suspended.

3. The method of claim 1, further comprising subjecting the resulting solution to 0.22 um aseptic filtration and 20 nm nano filtration for a first virus inactivation.

4. The method of claim 1, further comprising subjecting the resulting solution to filling and low pH incubation at pH 4 for 21 days at 25° C. as a second virus inactivation.

* * * * *